United States Patent [19]

Bowman et al.

[11] Patent Number: 5,233,197

[45] Date of Patent: Aug. 3, 1993

[54] HIGH SPEED DIGITAL IMAGING MICROSCOPE

[75] Inventors: Douglas Bowman, Shrewsbury; Fredric Fay, Worcester; Cyril Rodgers, Paxton; Richard Tuft, Bolton, all of Mass.

[73] Assignee: University of Massachusetts Medical Center, Worcester, Mass.

[21] Appl. No.: 729,978

[22] Filed: Jul. 15, 1991

[51] Int. Cl.$^5$ ........................ G01J 3/443; G01N 21/64
[52] U.S. Cl. .............. 250/461.1; 250/461.2; 356/417; 356/418
[58] Field of Search .............. 250/458.1, 459.1, 461.1, 250/461.2; 356/417, 418

[56] References Cited

U.S. PATENT DOCUMENTS

| | | | |
|---|---|---|---|
| 4,744,667 | 5/1988 | Fay et al. | 356/417 |
| 4,859,063 | 8/1989 | Fay et al. | 356/418 |
| 5,053,626 | 10/1991 | Tillotson | 250/458.1 |
| 5,149,972 | 9/1992 | Fay et al. | 250/461.1 |

OTHER PUBLICATIONS

Lasser-Ross, et al., "High time resolution fluorescence imaging with a CCD camera," *Journal of Neuroscience Methods*, 36 (1991), pp. 253-261.

O'Rourke et al, "High-Speed Digital Imaging of Cytosolic $Ca^{2+}$ and Contraction in Single Cardiomyocyts," *American Physiological Society*, pp. H230-H242.

Linderman et al., "Charge-Coupled Device Imaging of Rapid Calcium Transients in Cultured Arterial Smooth Muscle Cells," *Cell Calcium*, vol. 11, pp. 131-144, (1990).

Primary Examiner—Carolyn E. Fields
Attorney, Agent, or Firm—Hamilton, Brook, Smith & Reynolds

[57] ABSTRACT

A high speed fluorescent emission imaging digital microscope has an Argon-Ion UV laser illumination source and a high speed optical filtering wheel in the illumination path to alternately select between two UV illumination wavelengths to produce fluorescent emission images at each UV wavelength. A dichroic reflector directs emission images along an image path and an galvanometer rotatable mirror exposes each image on a predetermined area of a CCD. A computer controls the rotatable mirror in response to exposure timing information from the filtering wheel. An objective lens is focused on the specimen for producing an image from a particular focal plane of the specimen. The objective lens is mounted on a counterweighted piezoelectric objective translator for changing the focal plane of the specimen image in response to control signals from the electronic processor.

37 Claims, 8 Drawing Sheets

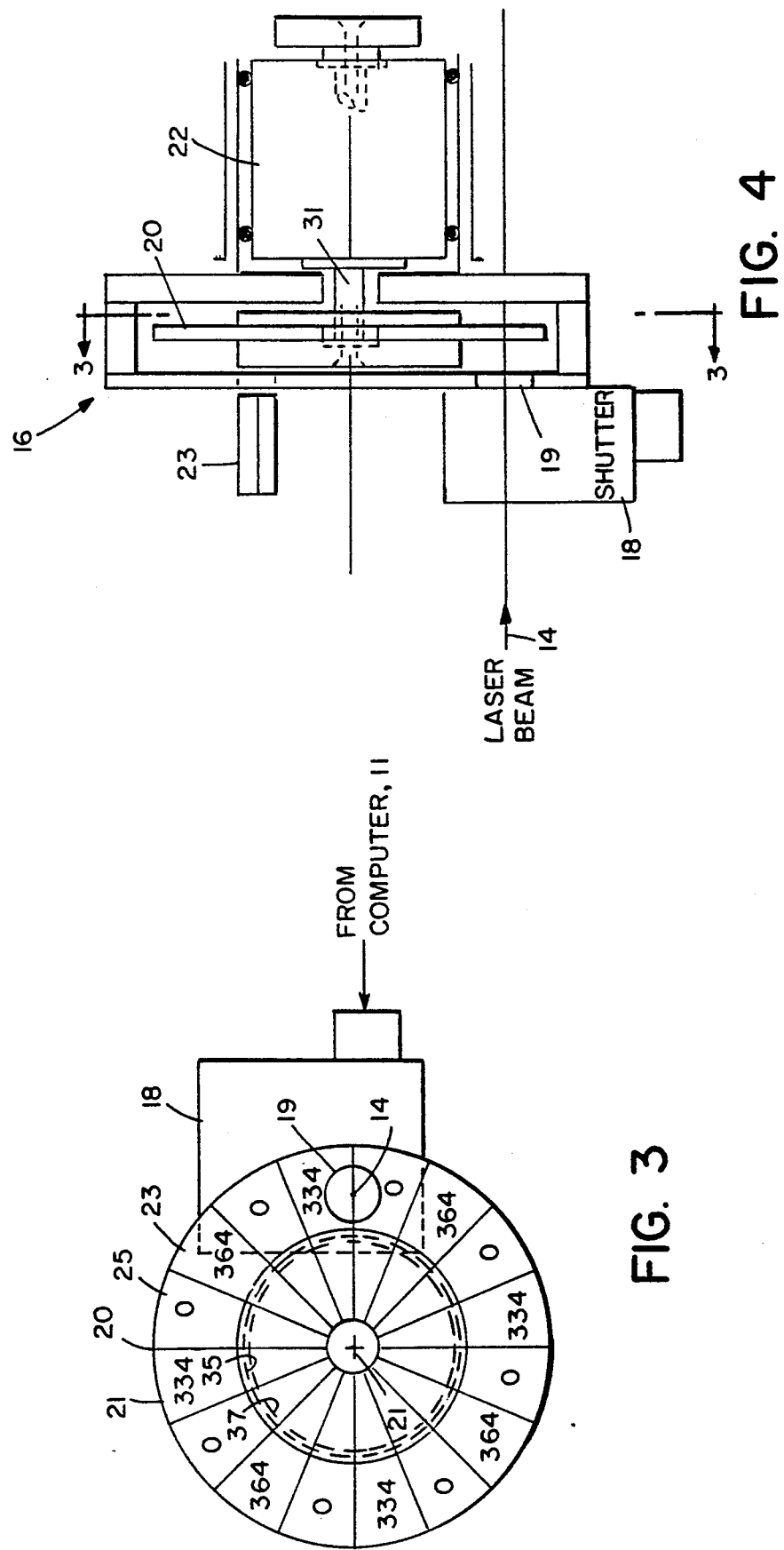

HIGH SPEED DIGITAL IMAGING MICROSCOPE

GOVERNMENT SUPPORT

The invention described herein was supported in whole or in part by Grant No. DIR-8720188 from the United States National Science Foundation.

BACKGROUND OF THE INVENTION

In scientific research, a material can often be characterized by the response of a fluorescent probe to radiation. In some procedures, a sample is illuminated alternately with light of different wavelengths and the fluorescence of the sample with the different illuminating wavelengths is noted. For example, the calcium ion is believed to control a variety of cellular processes with a high degree of spatial and temporal precision. Calcium has been measured in single living cells with high spatial resolution utilizing a microscope and highly fluorescent calcium sensitive dye Fura-2. A sample to which the dye has been added is illuminated alternately with two ultraviolet (UV) wavelengths, on of less than 360 nanometers (nm) and one of greater than 360 nm. In many current applications the illumination source is a Xenon lamp filtered to provide UV illumination at 340 nm and 380 nm. The free fluorescent dye fluoresces at about 500 nanometers maximally in response to the 380 nanometer excitation; whereas, the dye associated with the calcium ion fluoresces at about 500 nanometers maximally in response to the 340 nanometer excitation. The concentration of calcium can then be calculated from the formula:

$$[Ca^{++}]_i = K_d[(R-R_{min})/(R_{max}-R)]\beta$$

where $K_d$ is the effective dissociation constant for the Fura-2-Calcium reaction. R is the ratio of fluorescent intensity at 500 nm with the 340 and 380 nm excitation, $R_{min}$ is the limiting value of R at a calcium concentration of zero, $R_{max}$ is R with fully saturated calcium and $\beta$ is an optical constant for the system which is a measure of the relative quantum yield at 380 nm of the calcium free and calcium saturated dye.

Often, the distribution of the fluorescent probe or the ratio of the distribution of the probe in its free form relative to its distribution in a bound form within a sample is of interest. For example, the concentration of calcium ions is found to be greater in the cell nucleus than in the cytoplasm. The locations of the ion concentrations have been determined by taking successive two-dimensional images of a sample through incremental focus planes.

The orientation as well as the location of microscopic material may also be significant. For example, alpha-actinin has been observed in muscle cells using fluorescently labeled antibodies specific to alpha-actinin. The location and orientation of the oblong-shaped bodies can be determined by observing the images from plural sections of a sample.

An imaging microspectrofluorimeter for providing successive two dimensional images needed to generate high-resolution 3 dimensional (3D) microscope images has been described in U.S. Pat. No. 4,895,063, assigned to the assignee of the present application. The device there described has a maximum image rate of one image every five to six seconds, which is sufficient for studying biological specimens where the internal organization of the specimen does not appreciably change during the many seconds it takes to acquire a complete set of 2 dimensional images. Images of faster biological processes are therefore not possible with the device there described.

SUMMARY OF THE INVENTION

The present invention provides a high speed digital microscope having an imaging rate high enough to acquire sufficient 2 dimensional images taken at alternating wavelengths and in multiple image planes to furnish one high resolution image plane in 10 to 20 milliseconds. This high image acquisition rate provides a microscopic picture of internal cellular organization which "freezes" any rapidly varying changes such as diffusion of chemical messengers, e.g., Calcium, or the motion of organelles such as mitochondria.

In general, on one aspect, the invention provides a fluorescent emission imaging microscope including a UV radiation source radiating along an illumination path directed toward a specimen. An optical filtering device is placed in the illumination path to alternately select between two UV illumination wavelengths to produce fluorescent emission images at each UV wavelength. An image director directs the emission images along an image path and an image positioner exposes each image on a predetermined area of an imaging medium to store the images. An electronic processor automatically controls the image positioner in response to exposure timing information from the filter device.

Preferred embodiments include an Argon-Ion laser UV radiation source having major UV spectral lines at 334, 351, and 364 nm. The filter device includes radial bandpass filter sections having pass bands of 334 and 364 nm alternately arranged around a filter axis offset from the illumination path. Opaque sections are arranged between each of the filter sections to provide a blanking interval between alternating filter sections. A motor rotates the filter sections through the illumination path so that each filter section remains in the illumination path for between 0.5 and 5 milliseconds. An optical shutter is provided in the illumination path and synchronized to the rotating filters to chop the illumination passing through each filter section. A photometer measures the illumination used for generating each specimen image and feeds the measurement back to the electronic processor.

In other preferred embodiments the image director is a dichroic reflector for reflecting the UV illumination along the illumination path toward the specimen and allowing the transmission of the image from the specimen along the image path. The image positioner is a galvanometer rotatable mirror controlled by the electronic processor.

In yet other preferred embodiments the imaging medium is a charged coupled device having an unmasked area for storing specimen images arranged by the image positioner, and a masked area for storing specimen images transferred from the unmasked area.

In still other preferred embodiments an objective lens is focused on the specimen for producing an image from a particular focal plane of the specimen. The objective lens is mounted on a piezoelectric objective translator for changing the focal plane of the specimen image in response to control signals from the electronic processor. The translator includes a load beam having the objective lens attached to one end of the beam and a counterweight attached to the other end. A piezoelectric translator element is attached to the loading center of the beam to translate the objective lens along the image path and change the focal plane. An eddy current sensor feeds back the position of the objective to the electronic processor.

Thus, the present invention offers the advantages of a simplified image path to the video subsystem to improve imaging efficiency, a masked CCD for high speed strip image acquisition, an intense UV laser illumination source for excitation of fluorphores reducing exposure times, a means for high speed selection of alternating illumination wavelengths, a balanced piezoelectrically translated microscope objective to enable rapid changes in the focal plane of the specimen being imaged, and a computer for automatically controlling the microscope operation.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 3 and 4 show a detail drawing of the filter wheel assembly of the microscope of FIG. 1.

DESCRIPTION OF THE PREFERRED EMBODIMENT

Figure 1:
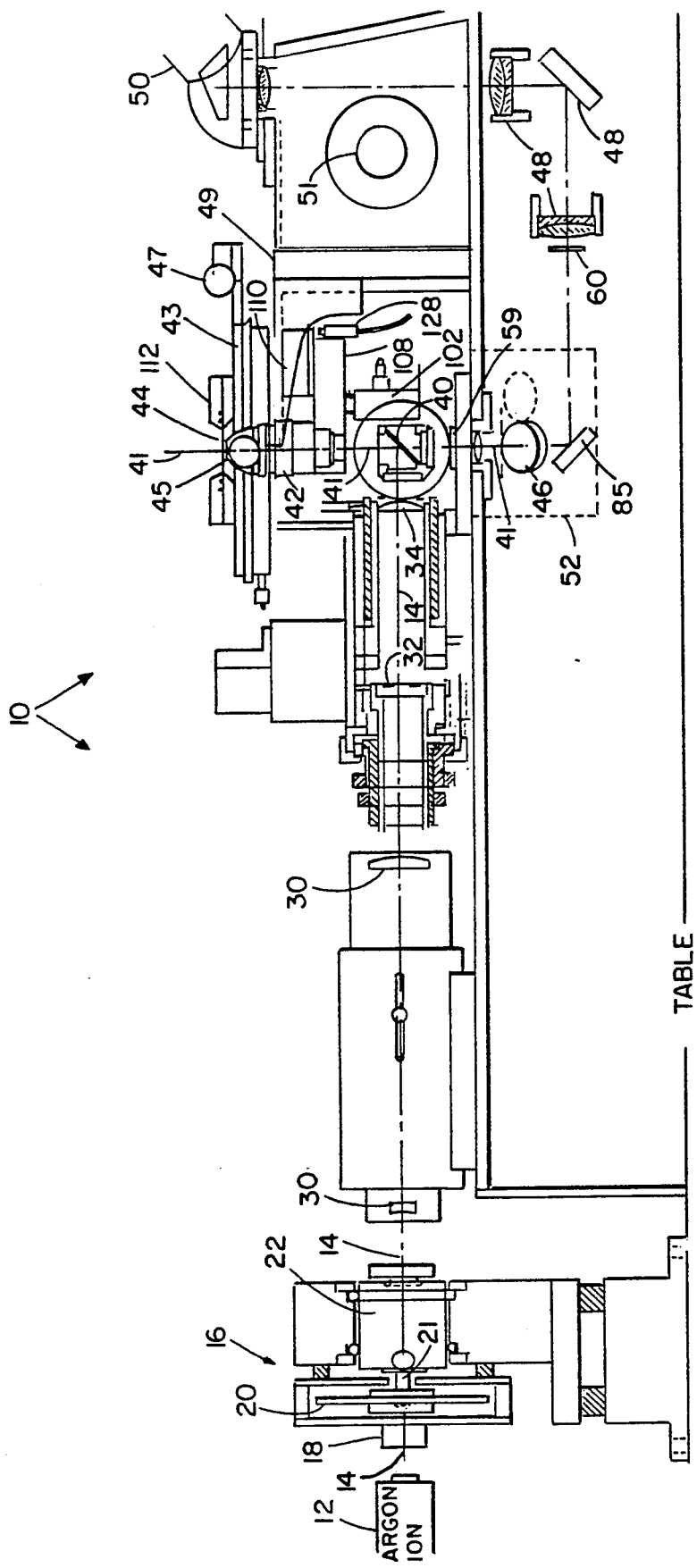
FIG. 1 is a cross-sectional view of the high speed digital imaging microscope of this invention.
Figure 2:
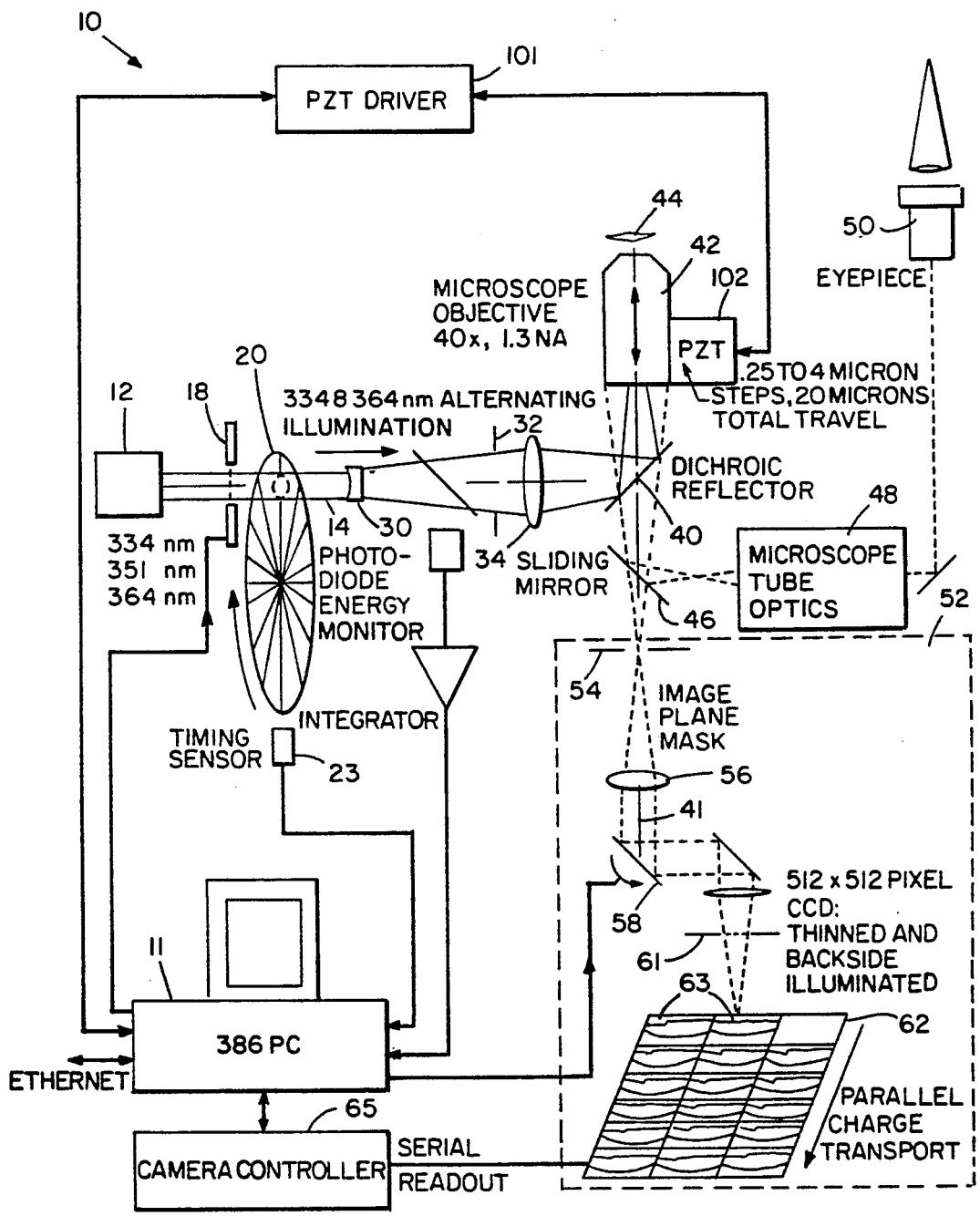
FIG. 2 is a system block diagram of the microscope of FIG. 1.

FIG. 1 shows a cross-sectional drawing and FIG. 2 shows a system block diagram of a high speed digital imaging microscope 10 capable of collecting multiple alternating wavelength emission images from multiple specimen focal planes, e.g., 1 ms exposures separated by 1 ms intervals. Microscope 10 is controlled by a computer 11 (FIG. 2), such as an 80386 based personal computer (PC), having analog and digital inputs and outputs for controlling the microscope system and to serve as a host for image acquisition and post-processing.

Digital imaging microscope 10 uses an Argon-Ion ultra-violet (UV) optical laser 12 for producing a beam of high-energy laser illumination along the illumination path of the microscope, i.e., along an optical axis 14. Argon-Ion laser 12 produces three strong UV spectral lines at 334, 351, and 364 nanometers (nm), each having an illumination power output of approximately 200 milliwatts.

The laser illumination radiated along optical axis 14 is controlled by a fast electro-mechanical shutter 18 connected to and controlled by computer 11 and having a 1 ms minimum open interval. A suitable electro-mechanical shutter is commercially available from Vincent Associates, 1255 University Ave., Rochester, N.Y. 14607 as the "Uniblitz" Model LS2 shutter and D122 shutter drive.

Laser illumination radiates through the open shutter and into a filter wheel assembly 16 (FIG. 1) where it impinges on a filter wheel 20 which introduces alternating optical and opaque filters into the path of the laser illumination.

Referring to FIGS. 3 and 4, a detail drawing of filter wheel assembly 16 shows that filter wheel 20 has a total of sixteen equal radial sections: four 334 nanometer bandpass filter sections 21 alternating with four 364 nanometer bandpass filter sections 23 separated by eight opaque sections 25. When filter wheel 20 is rotated, the laser illumination along optical axis 14 is chopped by the filter wheel filters to produce alternating laser illumination pulses, of equal duration, at 334 and 364 nm separated by a blanking interval having the same duration as each illumination pulse.

Other embodiments may use means other than the rotating filter wheel just described for selecting the illumination wavelengths. For instance, a fast tuning Fabry-Perot interferometer or Acousto-Optical tunable filters can provide the rapid wavelength selection required.

Shutter 18 has a shutter aperture 19 centered along the illumination path optical axis 14 which is offset from the center of the filter wheel 20 so that each filter section may fully cover the aperture for a predetermined period of time. Filter wheel 20 is mounted and dynamically balanced on the shaft 31 of a D.C. motor 22 which rotates the filter wheel at a high rate of speed, e.g, the filter wheel has been rotated as fast as 16 milliseconds per revolution. At 16 milliseconds per revolution, each of the filter sections passes across shutter aperture 19 during a one millisecond interval, i.e., the rotating filter wheel produces a one millisecond illumination pulse (exposure time for each image) at each wavelength separated by a one millisecond blanking interval. The wheel may also be rotated at other speeds to generate different image exposure and blanking time intervals., e.g., slower speed will generate longer time intervals.

A dual photo diode timing sensor 23 (FIG. 2) senses the rotation of the filter wheel according to a series of offset coding marks 35 and 37 imprinted on the filter wheel and feeds this timing information to computer 11 to control the microscope imaging sequence as discussed below. The coding marks allow the computer to detect if the wheel is currently producing a blanking interval or a filter interval, when a new filter is put into the illumination path, and the filter type. Here, the detection of coding mark 35 indicates to the computer that an opaque section is currently in the illumination path. The detection of coding mark 37 indicates to the computer that a 334 nm filter is currently in the illumination path. The absence of a coding mark indicates to the computer that a 364 nm filter is currently in the illumination path.

Other embodiments use a photodiode to detect a single timing mark on the filter wheel, rather than coding each of the filter sections as described above. This method proves sufficient for exposure timing purposes where the rotational speed of the wheel remains relatively stable. In this case, all exposure timing information is derived from the single timing pulse generated per revolution of the wheel.

Thus, the laser illumination output from filter assembly 16 along optical axis 14 contains alternating one millisecond 334 and 364 nm pulses each separated by a one millisecond blanking period during which no laser illumination is output from the filter assembly.

Referring again to FIG. 1, the laser illumination pulses output from filter assembly 16 traverse optical axis 14 passing through fused silica expansion optics 30, field stop lens diaphragm 32, and condensing optics 34. The illumination pulses then impinge on dichroic reflector 40 which is situated at a 45 degree angle to optical axis 14 and reflects the converging illumination pulses at a 90 degree angle along another optical axis 41 and through a high numerical aperture (NA) microscope objective 42 which protrudes through the center opening of a microscope stage 43 to illuminate the specimen 44.

Specimen 44 is held in an open top modified chamber 112 (discussed in detail below) which is horizontally positioned on stage 43 by standard X and Y vernier controls 45 and 47, respectively. The vertical position of the stage 43 is controlled by a standard rack and pinion adjuster 49 controlled by adjustment knob 51.

Stage 43 is rotatable about its central opening, i.e., rotatable about optical axis 41, so that the specimen may be aligned as desired. For instance, a typical muscle cell to be imaged has an elongated shape, and the digital video images to be acquired may have a rectangular field shape matching the shape of the cell to more efficiently store the video images. Rotating stage 43 facilitates aligning the muscle cell to be imaged with the rectangular video field.

Each pulse of laser illumination impinging on specimen 44 produces a fluorescent emission image which passes along optical axis 41 back down through microscope objective 42 and passes through dichroic reflector 40 with little or no loss of emission image intensity. As discussed above, the UV laser illumination pulses at 334 and 364 nm cause the specimen to produce a fluorescent emission image at approximately 500 nm, i.e., visible light. Dichroic reflector 40 has a transmission curve which is wavelength dependent, i.e., UV reflective and non-UV transmissive, and effectively separates the UV illumination pulses in the illumination path from the non-UV emission image in the emission image path according to wavelength. Thus, the emission image from sample 44 can pass through dichroic mirror 40 and continue along optical axis 41 toward the remainder of the microscope imaging system. A suitable dichroic reflector is commercially available from Omega Optical Inc., 3 Grove St., Brattleboro, Vt. 05301 as model 400 DCLP.

As shown, objective 42 in this high speed digital imaging microscope plays the double role of an illumination condenser for directing laser illumination pulses toward the specimen, and magnifying lens for imaging the fluorescent emissions from the specimen. It is a critical component of the optical system and it should be free of chromatic aberrations and have a high numerical aperture (NA), which is the figure of merit for the objective and defined as:

$$NA = n' \sin(\theta)$$

where n' is the refractive index of the medium and $\theta$ is the half angle of collection. A suitable objective with a numerical aperture of 1.3 is commercially available from Nikon Inc., 1300 Walt Whitman Rd., Melville, N.Y. 11747, as model C F Fluor 40x, NA 1.3. Objective 42 uses an immersion fluid, such as oil or glycerin, between the objective lens and the sample cover slip. The image collection efficiency here is proportional to the fourth power of the numerical aperture, which indicates its importance in light limited situations such as the high speed emission imaging of living single cells.

After the fluorescent emission from specimen 44 passes through dichroic mirror 40 along optical axis 41 the emission image passes through an interference filter 59 which removes UV interference from the image. The bandpass of the interference filter is centered at the peak emission wavelength of the fluorescent probe and has a bandwidth narrow enough to minimize any UV leak from the illumination path. The interference filter also increases the emission image signal-to-noise ratio (SNR) by eliminating signals from other sources such as cell auto fluorescence.

The actual bandwidth of the interference filter is a compromise between rejection of unwanted signals (auto fluorescence), and efficient collection of the fluorescent probe emissions. The auto fluorescent signal typically peaks around 400 nm and diminishes rapidly with increasing wavelength. A typical interference filter has a bandpass centered at 510 nm having a half power bandwidth of 40 nm. A suitable interference filter is commercially available from Omega Optical Inc. as model 510 WB 40.

After the fluorescent emission from specimen 44 passes through interference filter 59 along optical axis 41 the emission image may optionally take one of two optical paths determined by a sliding mirror 46. When the operator removes sliding mirror 46 from the image path along optical axis 41, a fixed mirror 85 reflects the emission image through a set of standard microscope tube optics 48 and to a binocular eyepiece 50 for visual microscopy. When the operator places the sliding mirror 46 into the emission image path along optical axis 41 the emission image is instead directed to video imaging subsystem 52 (CCD Camera shown in phantom in FIG. 1). A suitable CCD camera and controller is commercially available from Photometrics Ltd., 3440 East Britannia Dr., Tucson, Ariz. 85706, as model CH 250 (camera) and CC 200 (controller).

In the case where the emission image is directed by sliding mirror 46 to the binocular eyepiece for visual microscopy, an alignment reticle 60 is placed in the emission image path after fixed mirror 85 and before the binocular eyepiece. The alignment reticle, which may be a cross-hair or rectangular area type, is used to align the specimen image for the video imaging subsystem 52, i.e., visually position the specimen using the XY controls 45, 47 and by rotating the stage 43 so that the specimen will be aligned within the video image field.

Video imaging subsystem 52 (FIG. 2) has an image plane mask 54 placed at an intermediate image plane along the optical path of the emission image which limits the area of the transmitted image field, i.e., the mask crops the area of the emission image. The mask is placed at an intermediate image plane to produce a sharp edge around the transmitted image field.

The area-limited emission image then passes through a set of convergence optics 56, and is reflected by a galvanometer rotatable mirror 58 through a shutter 61 and onto a charge coupled device (CCD) imager 62. The CCD is divided into sub-image areas 63 each capable of storing one area-limited emission image field. The shape of each sub-image area is determined by the image plane mask 54 and typically has an elongated rectangular shape.

Computer 11 is coupled to the galvanometer rotatable mirror and causes the mirror to direct the converging emission image field to impinge on a desired sub-image area of the CCD. Between emission image exposures, the position of the emission image field on the CCD is moved along the row direction to another sub-image area at the top of the CCD by the galvanometer mirror. When the image fields fill the top row of sub-image areas, these accumulated sub-images are rapidly shifted by parallel charge transport to the masked region of the CCD, where they are stored. The top row of sub-image areas are then available to store the next sequential series of emission sub-image fields.

The serial image read out from the CCD goes to a camera controller 65 coupled to computer 11 which acts as an interface between the CCD and the computer. The camera controller includes its own processor and memory for storing and manipulating the image received from the CCD. The controller shown here has 8 MBytes of image cache RAM, is connected to the computer via an IEEE-488 interface, and responds to FORTH commands issued by the computer. Once the image is received by the controller, it is transferred to the computer as requested by the computer. In other embodiments, a camera controller is not necessary where computer 11 has enough processing power and memory to receive images directly from the CCD.

Figure 5A:
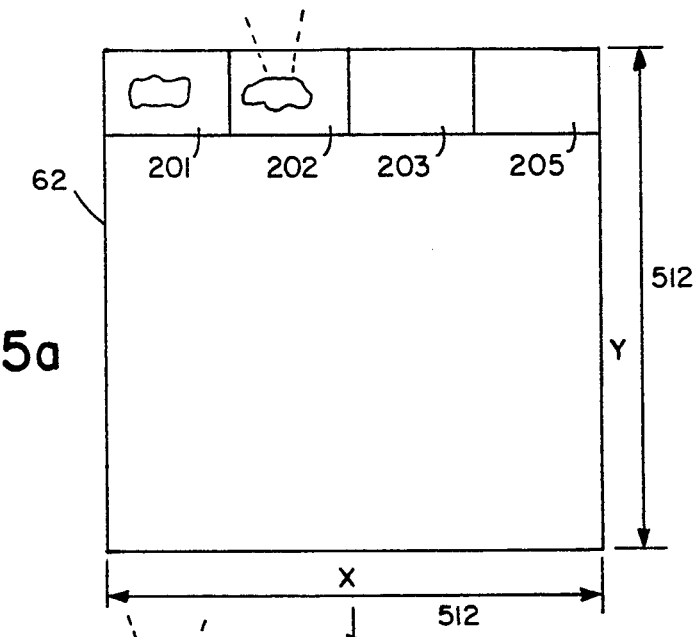
FIGS. 5(a)-5(c) show a sequence illustrating image storage on the video CCD of the microscope of FIG. 1.
Figure 5B:
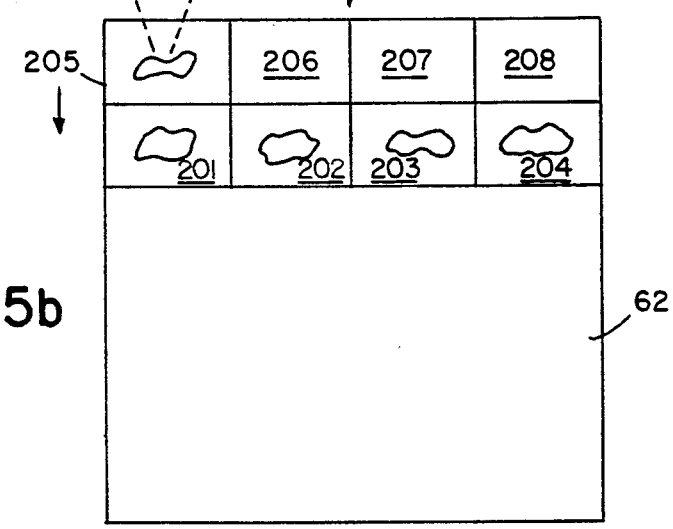
Figure 5C:
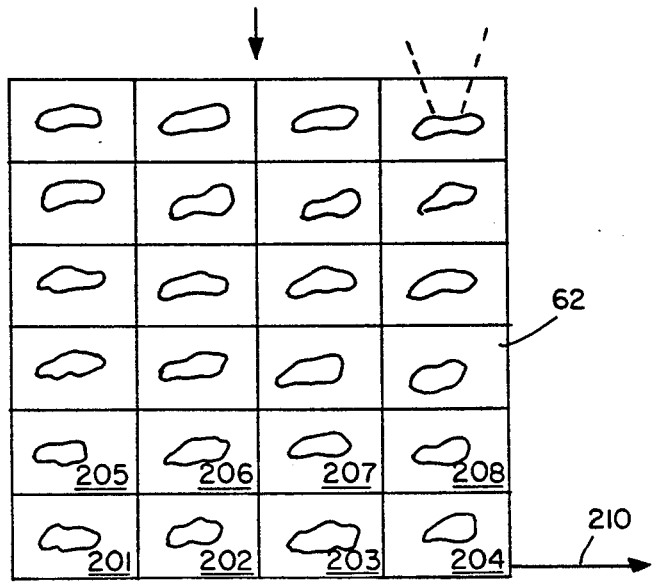

FIGS. 5(a)–5(c) illustrate in detail the rapid formation of multiple emission images on CCD 62. CCD 62 in this case has 512 pixels in the X and 512 pixels in the Y direction. The CCD is exposed with a sequential series of area-limited emission images each corresponding to a separate exposure of the specimen by a UV illumination pulse of approximately 1 ms duration generated by the rotating filter and electro-mechanical shutter in the laser light illumination path. As shown in FIG. 5(a), a first image 201 is formed on a sub-image portion 63 of the CCD starting in the upper left hand corner of the device. Computer 11 repositions the galvanometer rotatable mirror between laser illumination pulses, i.e., during the blanking period, so that the next image 202 is positioned on the sub-image area horizontally adjacent to and not overlapping first sub-image area storing emission image 201. Computer 11 continues to reposition the galvanometer rotatable mirror so that subsequent images are swept horizontally across the CCD, e.g., placing the next two images in CCD sub-image areas and 204 respectively.

Once a full row of sub-images 201–204 have been accumulated on the CCD 62, that row of sub-images is shifted vertically along the Y direction using parallel charge transport mechanism of the CCD resulting in the configuration shown in FIG. 5(b). Subsequent emission images are sequentially stored in CCD sub-image areas 205, 206, 207, and 208 as the galvanometer rotatable mirror again sweeps the images horizontally across the CCD so that each adjacent image is horizontally adjacent to the previous image and not overlapping it.

After the row of adjacent images 205–208 is accumulated all the accumulated sub-images are again shifted along the Y direction by the parallel charge transport mechanism and more images are accumulated along the top row of the CCD until the CCD is full as shown in FIG. 5(c). Once the CCD is full, the sub-images are serially read out 210 from the CCD to the camera controller for reconstruction by computer 11. A good emission image signal-to-noise ratio (SNR) is obtained from the CCD by first filling the entire CCD with sub-images and then slowly serially reading the images out from serial read out port 210.

Figure 8:
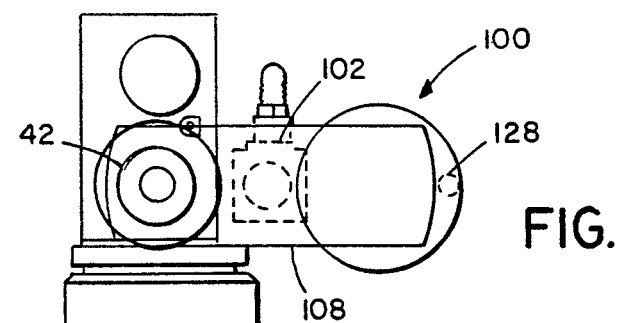
FIGS. 6-8 show detail drawings of the high speed objective translator of the microscope of FIG. 1.
Figure 6:
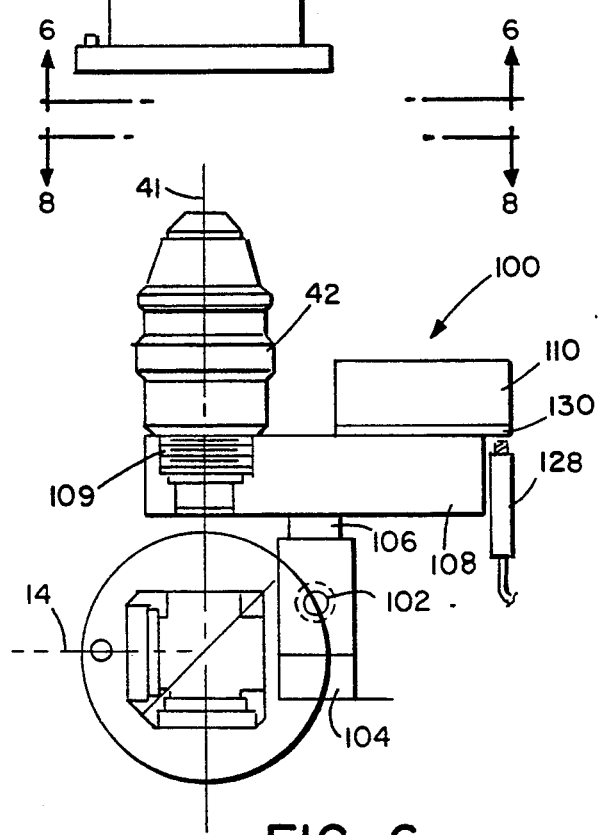
Figure 7:
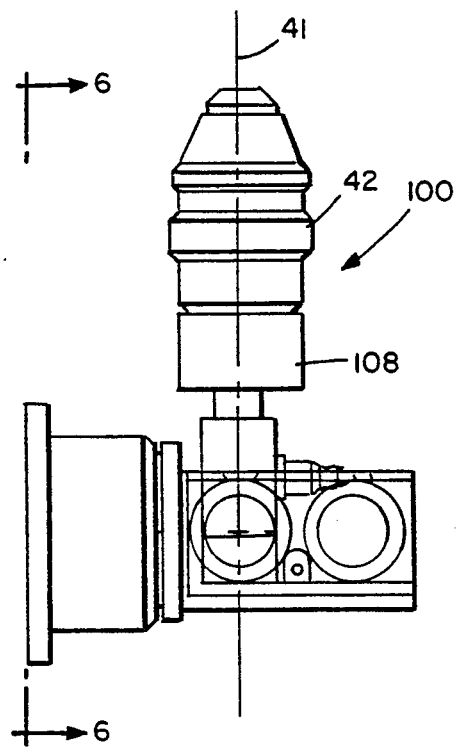

FIGS. 6–8 show details of the microscope objective 42 mounted on a dynamically balanced objective translator 100 which can rapidly change the specimen focal plane for producing high speed 3D emission images. The dynamically balanced translator shown is capable of translating the microscope objective several micrometers in 1 ms or less total translation and settling time. The objective translator uses a piezoelectric (PZT) translator 102 having a 20 micron total travel mounted on one end 104 to the stationary base of the microscope. The other end 106 of the PZT translator 102 is connected to the loading center of a cast iron load beam 108. Cast iron is a preferred material for load beam 108 due to its favorable mechanical damping characteristics. Objective 42 is threadably attached into an aperture 109 in one end of the load beam and aligned with optical axis 41. A counter weight 110 is attached to the opposite side of the beam to counter balance the weight of the objective 42 and thereby precisely position the loading center of the load beam at the PZT translator.

Computer 11 is coupled to the PZT translator through a PZT driver circuit 101 which receives commands from the computer and in response produces electrical voltages to stimulate the PZT driver. With this configuration and by electrically stimulating PZT translator 102 to alternately push and pull against the load center of load beam 108, objective 42 is rapidly translated along optical axis 41 and quickly settles at its new position, i.e. focal plane, in less than 1 ms. A suitable PZT translator and driver is commercially available from Polytec Optronics, 3001 Red Hill Ave., Costa Mesa, Calif. 92626 as model P-244.27 (translator) and P-267.00 (driver).

An eddy current sensor 128, coupled to computer 11, is mounted adjacent to the counterweight 110 to precisely determine the position of the objective relative to the specimen. Eddy current sensor 128 senses eddy currents induced in an aluminum plate 130, mounted under the counterweight, by the movement of objective translator load beam 108 (or the objective lens 42) relative to the sensor (or the specimen) and provides a feedback signal to computer 11 indicating the position of the objective 42 with respect to the specimen. This allows computer 11 to precisely determine the position of the objective as it commands the PZT translator movements and thereby rapidly focus the objective at each new focal plane.

Figure 9:
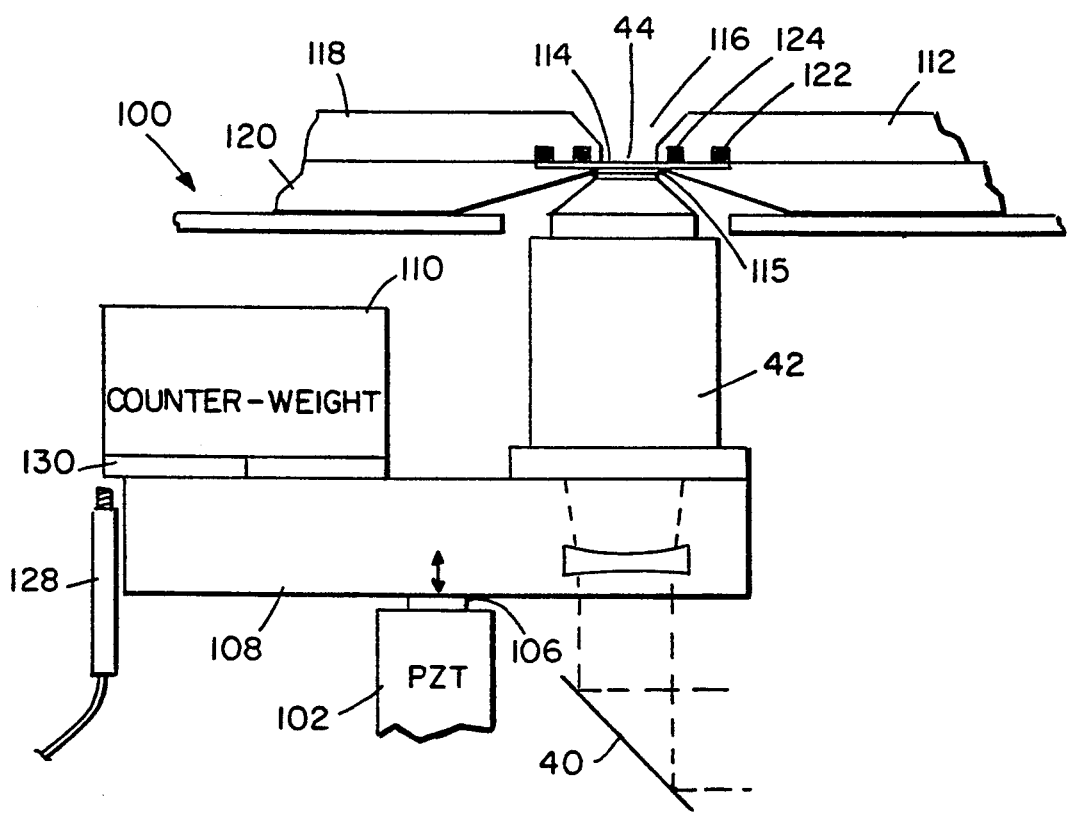
FIG. 9 shows a detail drawing of the modified specimen chamber used with the high speed objective translator of FIGS. 6-8.

FIG. 9 shows the dynamically balanced objective translator 100 used in conjunction with a modified "stiff" chamber 112 for holding specimen 44. A cover glass 114 is positioned in the chamber well aperture 116 and sandwiched between an upper chamber portion 118 and a lower chamber portion 120. Objective 42 is optically coupled to the underside of the cover glass 114 through a layer of immersion oil 115 having a nominal oil gap of 220 micrometers. Since the objective is mechanically coupled to the cover glass through a layer of oil, rapid movements of the objective cause the cover glass of a standard chamber (typically held in place with a single 0.9 inch diameter o-ring) to flex as the oil tries to escape a narrowing gap or fill an increasing gap. Cover glass flexing reduces the performance of the high speed objective translator 100 since extra time is required for the cover glass to settle to its original preflexed state.

Modified "stiff" chamber 112 effectively eliminates cover glass flexing. Cover glass 114 is stiffly held in place by an outer rubber o-ring 122 having a 0.9 inch diameter (like the standard chamber), and additionally by an inner rubber o-ring 124 having a 0.45 inch diameter. Each o-ring is disposed in a corresponding annular channel cut into the upper chamber portion 118. The smaller exposed cover glass area along with the inner and outer o-ring mounting of the modified chamber 112 provides significantly greater stiffness over the standard chamber cover glass and prevents unsatisfactory flexing during rapid movement of the objective 42 relative to the glass, and thus rapid objective settling times are achieved.

Figure 10:
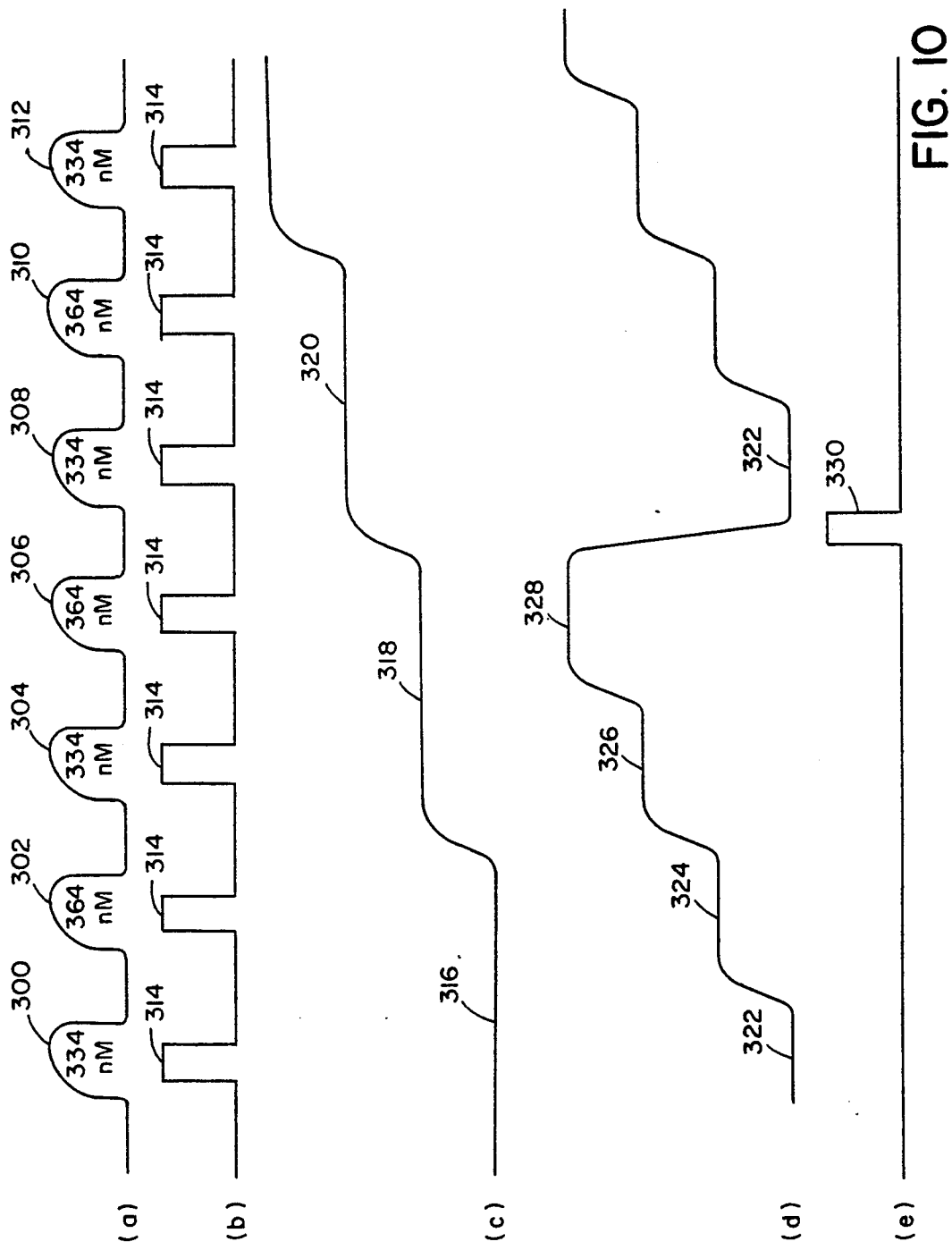
FIG. 10 is a timing diagram illustrating the operation of the microscope of FIG. 1.

FIG. 10 shows a timing diagram of a typical two excitation wavelength emission image collection by the high speed digital microscope of this invention. Trace (a) represents the output from filter wheel 20 showing laser illumination pulses having alternating wavelengths of 334 and 364 nm, separated by blanking intervals. Each laser illumination pulse 300 through 312 has a slightly different illumination pulse characteristic since each is created by illumination through a different filter element, i.e., there would be a slightly different filter characteristics for each of the four filters associated with each wavelength since each filter section experiences a slightly different edge characteristic as the filter wheel rotates from an opaque section to the filter section.

Trace (b) shows the drive pulse for electro-mechanical shutter 18 whose open period, indicated by the pulses 314, is positioned in the center of each illumination pulse 300-312 to pass only the most uniform portion of each illumination pulse, i.e., mask the rising and falling edge of each pulse.

Even though the laser illumination pulses of trace (a) are chopped by the shutter pulses of trace (b), the illumination of the specimen by any given illumination pulse is likely to be slightly different than illumination by another illumination pulse. A photo diode energy monitor 66 monitors the intensity of each illumination pulse, and an integrator 68 integrates the illumination energy during each pulse and feeds the integrator result to computer 11 which uses the result to normalize the image intensities during quantitative image analysis.

Trace (c) represents the control voltage output from PZT driver 101 and applied to the PZT translator 72 of objective translator 70 to position objective 42 at the desired focal plane of specimen 44. As shown, the fluorescent emission images exposed by alternating wavelength laser illumination pulses 300 and 302 are taken at a first focal plane determined by PZT voltage 316 shown in trace (c). The next two emission images exposed by illumination pulses 304 and 306 are taken at a different focal plane as determined by PZT voltage 318 shown in trace (c). Similarly, each subsequent set of alternating wavelength emission images are taken at a slightly different focal plane determined by changing the voltage applied to PZT, i.e., emission images exposed by illumination pulses 308 and 310 are taken at a focal plane determined by PZT voltage 320, etc..

Trace (d) represents the control voltage applied by computer 11 to rotatable galvanometer mirror 58 to sweep each sequential emission image across the top row of the CCD of FIG. 5(a)-5(c). Galvanometer control voltage level 322 positions the galvanometer mirror to expose the top left sub-image section of the CCD, such as sub-image 201 of FIG. 5(a). Similarly galvanometer control voltage 324 corresponds to exposing sub-image 202 of FIG. 5(a), 326 corresponds to sub-image 203 and 328 corresponds to sub-image 204.

After the last sub-image of the first CCD sub-image row is exposed, e.g., sub-image 204 of FIG. 5(a), the galvanometer control voltage is returned to level 322 which corresponds once again to the leftmost sub-image area of the first CCD sub-image row, e.g., sub-image 201 of FIG. 5(a), and the process is repeated for the next sequential images.

Trace (e) shows a CCD parallel charge transport control pulse 330 produced by computer 11 which causes the CCD to shift all the CCD image rows in the Y direction as shown in FIG. 5(b). As shown this control pulse is generated during the galvanometer mirror retrace time between voltage level 328 and voltage level 322 of trace (d).

Many alternative operational timing schemes are possible, depending on the particular embodiment. For instance, in one alternative embodiment trace (a) could represent constant laser illumination at a single wavelength and the shutter pulses of trace (b) would chop the constant illumination to produce illumination pulses at the same wavelength. In this case, the galvanometer control voltage of trace (d) could remain the same, but the PZT control voltage of trace (c) could change to alter the focal plane for each new illumination pulse rather than illumination pulse pairs. In another alternative embodiment the shutter could be left open, i.e., trace (b) would be a constant, and the alternating wavelength laser illumination pulses of trace (a) would illuminate the target to produce emission images. No other timing changes would be required.

Figure 11:
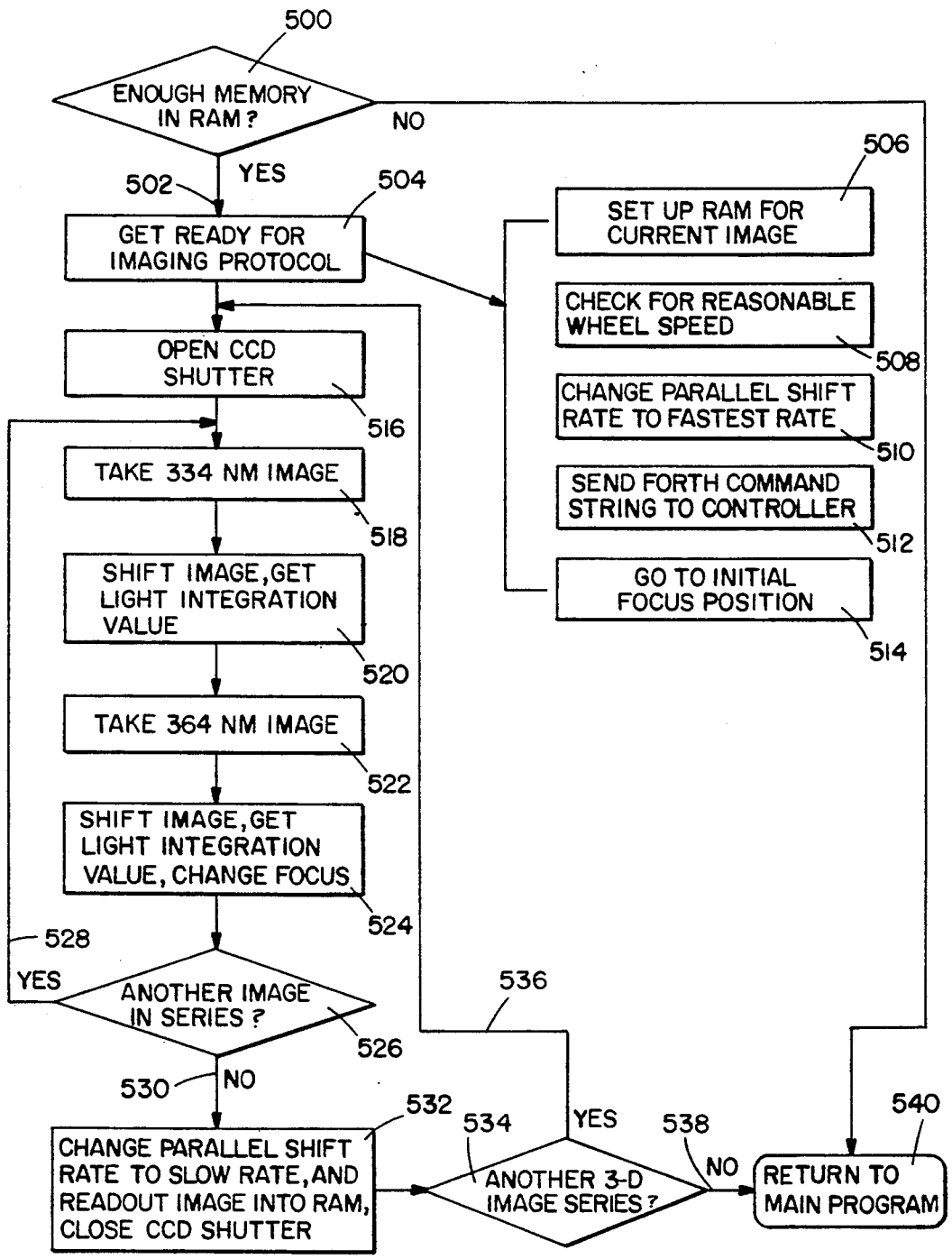
FIG. 11 is a flow diagram illustrating a computer program for automatically controlling the microscope of FIG. 1.

FIG. 11 shows a flow chart of a computer program run on computer 11 for controlling the alternating wavelength multiple focal plane imaging protocol of the high speed digital imaging microscope of this invention. When imaging is desired, a main program, e.g., a menu driven microscope controller, invokes the imaging protocol software which first determines 500 if there is enough memory available in the computer RAM to store the images about to be accumulated in the CCD. Once it is determined 502 that enough memory is available for the desired imaging protocol, the digital microscope control system is initialized 504 by setting up the RAM for the current image 506, checking the filter wheel speed 508, changing the parallel shift rate of the CCD to the fastest rate available 510, and sending 512 a command string to the camera controller 65 (FIG. 2) and initializing 514 the PZT translator to position the objective translator at an initial focal plane.

Once initialization is complete, the CCD is exposed 516 by opening a CCD shutter 61 (FIG. 2) in the video subsystem 52 (CCD camera). A 334 nm emission image is exposed 518 first on the CCD, the sub-image position is shifted by the rotating galvanometer mirror during the blanking interval, and the light integration value of illumination pulse used to expose the image is determined 520 and stored by the computer for later normalization of the image intensity. Next a 364 nm emission image is exposed 522 on the CCD, the sub-image position is again shifted by the rotating galvanometer mirror during the next blanking interval, and the light integration value of illumination pulse used to expose the image is determined and stored by the computer for later normalization of the image intensity, and the focal plane of the system is changed by adjusting 524 the PZT translator control voltage.

Next it is determined 526 if another alternating wavelength image series is desired. If another series is desired 528 then the process of taking alternating 334 and 364 nm emission images is repeated. If another image series is not desired 530 then the images stored in the CCD are read out 532 by slowing the parallel shift rate of the CCD, closing the CCD camera shutter, and serially reading the CCD image into the camera controller RAM for analysis by computer 11.

Finally, it is determined 534 if another 3D image series is desired. If another 3D series is desired 536 then the imaging protocol is repeated. If no new 3D image series is desired 538 then control is returned 540 to the main program.

While this invention has been particularly shown and described with reference to preferred embodiments thereof, it will be understood by those skilled in the art that various changes in form and details may be made therein without departing from the spirit and scope of the invention as defined by the appended claims. For instance, although the embodiments described herein used two specific wavelengths of illumination, the microscope is not limited to these specific wavelengths, and other illumination wavelengths may be used. Similarly, any number of illumination wavelengths may be alternated, i.e., the microscope may alter three or more illumination wavelengths. Further, the microscope may use only a single illumination wavelength chopped at a high rate to take a high speed succession of images at the same wavelength. Also, the microscope may be synchronized with electrical biological stimulation to enable high speed imaging of processes induced by the stimulation.

We claim:

1. A fluorescent emission imaging microscope, comprising
    a UV radiation source for radiating a plurality of illumination wavelengths along an illumination path;
    an optical filtering device placed in the illumination path for selecting a first and a second illumination wavelength from the plurality of illumination wavelengths and alternately illuminating a specimen to produce plural specimen images;
    an image director for directing the resulting specimen images along a specimen image path;
    an imaging medium placed in the specimen image path for storing a plurality of the specimen images;
    an image positioner placed in the specimen image path between the specimen and the imaging medium for directing each specimen image illuminated with an alternate wavelength to a sub-image area on the imaging medium for storing each specimen image separate from other stored specimen images; and
    an electronic processor for automatically controlling the image positioner in response to feedback from the filtering device.

2. The apparatus of claim 1 wherein the UV radiation source comprises a laser light source.

3. The apparatus of claim 2 wherein the laser light source comprises an argon-ion laser having major spectral lines at substantially 334, 351, and 364 nm.

4. The apparatus of claim 3 wherein said filtering device comprises at least one optical bandpass filter having a bandpass at 334 nm and at least one bandpass filter having a bandpass at 364 nm.

5. The apparatus of claim 1 wherein the optical filtering device comprises
    a plurality of radial bandpass filter sections having at least two pass bands arranged around a filter axis offset from the illumination path; and
    a motor coupled to the bandpass filter sections for rotating the filter sections through the illumination path.

6. The apparatus of claim 5 wherein the bandpass filter sections comprise a plurality of filter sections having a pass band at the first illumination wavelength arranged alternately with a plurality of filter sections having a pass band at the second illumination wavelength.

7. The apparatus of claim 6 wherein the filtering device further comprises a plurality of opaque sections arranged between each of the filter sections.

8. The apparatus of claim 6 wherein each of the radial passband filter sections rotated through the illumination path remains in the illumination path for a time interval between 0.5 and 5 ms.

9. The apparatus of claim 8 wherein the time interval is between 0.5 and 2 ms.

10. The apparatus of claim 1 wherein the image director comprises a dichroic reflector for reflecting the UV illumination along the illumination path toward the specimen and allowing the transmission of the image from the specimen along the image path.

11. The apparatus of claim 1 wherein the image positioner comprises a galvanometer rotatable mirror coupled to the electronic processor.

12. The apparatus of claim 1 wherein the imaging medium comprises a charged coupled device.

13. The apparatus of claim 12 wherein the charged coupled device comprises
    an unmasked area for receiving a plurality of specimen images from the image path and storing the received images as non-overlapping sub-images arranged on the charge coupled device by the image positioner; and
    a masked area for receiving and storing the plurality of specimen images transferred from the unmasked area.

14. The apparatus of claim 1 further comprising
    an objective lens positioned in the imaging path for focusing on the specimen and producing an image from a particular focal plane of the specimen;
    an objective translator coupled to the objective lens for translating the objective lens along the imaging path to change the focal plane of the specimen image, the objective translator comprising a piezoelectric translator coupled to the electronic processor for producing the objective lens translation in response to a control signal from the electronic processor.

15. The apparatus of claim 14 wherein the objective translator further comprises
    an elongated load beam having two ends and disposed substantially perpendicular to the image path, and having the objective lens attached to one end of the load beam; and
    a counterweight attached to the other end of the load beam to counterbalance the weight of the objective lens and to provide a center of loading on the load beam located between the counterweight and the objective lens;

wherein the piezoelectric translator is attached to the load beam at the center of loading such that the piezoelectric translator has a translation direction substantially parallel to the image path for translating the objective lens along the image path.

16. The apparatus of claim 15 further comprising an eddy current sensor positioned in the vicinity of the objective translator for sensing the position of the objective relative to the specimen, and coupled to the electronic processor for feeding back the objective position to the electronic processor.

17. The apparatus of claim 14 wherein the objective translator repositions the objective lens at a rate of about 1 micrometer per millisecond.

18. The apparatus of claim 1 further comprising
a photometer coupled to the electronic processor and to the illumination path for measuring the illumination used for generating each stored specimen image and feeding back a measured illumination value to the electronic processor,
wherein the electronic processor uses the measured illumination value to normalize each stored image intensity for analysis.

19. The apparatus of claim 18 wherein the photometer comprises an integrator for accumulating the total illumination for each stored image.

20. A fluorescent emission imaging microscope, comprising
a laser UV radiation source for radiating a plurality of illumination wavelengths along an illumination path;
an optical filtering device placed in the illumination path for selecting a first and a second illumination wavelength from the plurality of illumination wavelengths and alternately illuminating a specimen to produce plural specimen images;
an objective lens positioned in the imaging path for focusing on the specimen and producing an image from a particular focal plane of the specimen;
an objective translator coupled to the objective lens for translating the objective lens along the imaging path to change the focal plane of the specimen image, the objective translator comprising a piezoelectric translator;
an image director for directing the resulting specimen images along a specimen image path;
an imaging medium placed in the specimen image path for storing a plurality of the specimen images;
an image positioner placed in the specimen image path between the specimen and the imaging medium for directing each specimen image illuminated with an alternate wavelength to a sub-image area on the imaging medium for storing each specimen image separate from other stored specimen images; and
an electronic processor for automatically controlling the image positioner in response to feedback from the filtering device and for automatically controlling the objective translator to select a desired specimen image focal plane.

21. The apparatus of claim 20 herein the laser light source comprises an argon-ion laser having major spectral lines at substantially 334, 351, and 364 nm.

22. The apparatus of claim 21 wherein said filtering device comprises at least one optical bandpass filter having a bandpass at 334 nm and at least one bandpass filter having a bandpass at 364 nm.

23. The apparatus of claim 20 wherein the optical filtering device comprises
a plurality of radial bandpass filter sections having at least two pass bands arranged around a filter axis offset from the illumination path; and
a motor coupled to the bandpass filter sections for rotating the filter sections through the illumination path.

24. The apparatus of claim 23 wherein the bandpass filter sections comprise a plurality of filter sections having a pass band at the first illumination wavelength arranged alternately with a plurality of filter sections having a pass band at the second illumination wavelength.

25. The apparatus of claim 24 wherein the filtering device further comprises a plurality of opaque sections arranged between each of the filter sections.

26. The apparatus of claim 24 wherein each of the radial passband filter sections rotated through the illumination path remains in the illumination path for a time interval between 0.5 and 5 ms.

27. The apparatus of claim 26 wherein the time interval is between 0.5 and 2 ms.

28. The apparatus of claim 20 wherein the image director comprises a dichroic reflector for reflecting the UV illumination along the illumination path toward the specimen and allowing the transmission of the image from the specimen along the image path.

29. The apparatus of claim 20 wherein the image positioner comprises a galvanometer rotatable mirror coupled to the electronic processor.

30. The apparatus of claim 20 wherein the imaging medium comprises a charged coupled device.

31. The apparatus of claim 30 wherein the charged coupled device comprises
an unmasked area for receiving a plurality of specimen images from the image path and storing the received images as non-overlapping sub-images arranged on the charge coupled device by the image positioner; and
a masked area for receiving and storing the plurality of specimen images transferred from the unmasked area.

32. The apparatus of claim 20 wherein the objective translator further comprises
an elongated load beam having two ends and disposed substantially perpendicular to the image path, and having the objective lens attached to one end of the load beam; and
a counterweight attached to the other end of the load beam to counterbalance the weight of the objective lens and to provide a center of loading on the load beam located between the counterweight and the objective lens;
wherein the piezoelectric translator is attached to the load beam at the center of loading such that the piezoelectric translator has a translation direction substantially parallel to the image path for translating the objective lens along the image path.

33. The apparatus of claim 32 further comprising an eddy current sensor positioned in the vicinity of the objective translator for sensing the position of the objective relative to the specimen, and coupled to the electronic processor for feeding back the objective position to the electronic processor.

34. The apparatus of claim 20 wherein the objective translator repositions the objective lens at a rate of about 1 micrometer per millisecond.

35. The apparatus of claim 20 further comprising
a photometer coupled to the electronic processor and to the illumination path for measuring the illumination used for generating each stored specimen image and feeding back a measured illumination value to the electronic processor,
wherein the electronic processor uses the measured illumination value to normalize each stored image intensity for analysis.

36. The apparatus of claim 35 wherein the photometer comprises an integrator for accumulating the total illumination for each stored image.

37. A fluorescent emission imaging microscope, comprising
a laser UV radiation source for radiating a plurality of illumination wavelengths along an illumination path;
an optical filtering device placed in the illumination path for selecting a first and a second illumination wavelength from the plurality of illumination wavelengths and alternately illuminating a specimen to produce plural specimen images;
an objective lens positioned in the imaging path for focusing on the specimen and producing an image from a particular focal plane of the specimen;
an objective translator coupled to the objective lens for translating the objective lens along the imaging path to change the focal plane of the specimen image, the objective translator comprising a piezoelectric translator;
a dichroic reflector for directing the resulting specimen images along a specimen image path;
an charge coupled device placed in the specimen image path for storing a plurality of the specimen images;
a galvanometer rotatable mirror placed in the specimen image path between the specimen and the imaging medium for directing each specimen image illuminated with an alternate wavelength to a sub-image area on the imaging medium for storing each specimen image separate from other stored specimen images; and
an electronic processor for automatically controlling the galvanometer rotatable mirror in response to feedback from the filtering device and for automatically controlling the objective translator to select a desired specimen image focal plane.

* * * * *